(12) United States Patent
Kanaya et al.

(10) Patent No.: US 9,687,833 B2
(45) Date of Patent: Jun. 27, 2017

(54) METHOD OF PRODUCING OPTICALLY ACTIVE COMPOUND

(71) Applicant: DEXERIALS CORPORATION, Tokyo (JP)

(72) Inventors: Hiroki Kanaya, Utsunomiya (JP); Mamiko Nomura, Utsunomiya (JP)

(73) Assignee: DEXERIALS CORPORATION, Tokyo (JP)

( * ) Notice: Subject to any disclaimer, the term of this patent is extended or adjusted under 35 U.S.C. 154(b) by 0 days.

(21) Appl. No.: 14/777,649

(22) PCT Filed: Jun. 3, 2014

(86) PCT No.: PCT/JP2014/064770
§ 371 (c)(1),
(2) Date: Sep. 16, 2015

(87) PCT Pub. No.: WO2014/196542
PCT Pub. Date: Dec. 11, 2014

(65) Prior Publication Data
US 2016/0250625 A1  Sep. 1, 2016

(30) Foreign Application Priority Data

Jun. 5, 2013  (JP) ................................ 2013-119029
Jan. 10, 2014  (JP) ................................ 2014-003090

(51) Int. Cl.

| | |
|---|---|
| C07C 201/12 | (2006.01) |
| B01J 31/00 | (2006.01) |
| B01J 31/06 | (2006.01) |
| B01J 37/00 | (2006.01) |
| C07C 205/48 | (2006.01) |
| C07B 53/00 | (2006.01) |
| C07C 201/16 | (2006.01) |
| B01J 8/02 | (2006.01) |

(52) U.S. Cl.
CPC .............. B01J 31/062 (2013.01); B01J 8/02 (2013.01); B01J 31/06 (2013.01); B01J 37/00 (2013.01); C07B 53/00 (2013.01); C07C 201/12 (2013.01); C07C 201/16 (2013.01); C07C 205/48 (2013.01); B01J 2208/02 (2013.01); C07B 2200/07 (2013.01); C07C 2101/14 (2013.01)

(58) Field of Classification Search
CPC .......... C07C 201/12; B01J 31/062; B01J 8/02
USPC ....................................................... 568/306
See application file for complete search history.

(56) References Cited

U.S. PATENT DOCUMENTS

2002/0038042 A1  3/2002  Drauz et al.
2003/0187249 A1  10/2003  Jacobsen et al.
2004/0198591 A1  10/2004  Woltinger et al.
2007/0112199 A1  5/2007  Deng et al.
2007/0256736 A1  11/2007  Tonkovich et al.
2009/0227743 A1  9/2009  Hashimoto et al.

FOREIGN PATENT DOCUMENTS

| JP | 2002-095974 A | 4/2002 |
|---|---|---|
| JP | 2002-513734 A | 5/2002 |
| JP | 2002-275118 A | 9/2002 |
| JP | 2004-528174 A | 9/2004 |
| JP | 2008-501689 A | 1/2008 |
| JP | 2009-534179 A | 9/2009 |
| JP | 2010-248093 A | 11/2010 |
| JP | 2013-184973 A | 9/2013 |
| WO | 2008/013009 A1 | 1/2008 |

OTHER PUBLICATIONS

Notz et al., "Enamine-Based Organocatalysis with Proline and Diamines: The Development of Direct Catalytic Asymmetric Aldol, Mannich, Michael, and Deils-Alder Reactions," Accounts of Chemical Research, Aug. 2004, vol. 37, No. 8, pp. 580-591.

Kristensen et al., "Synthesis of Acrylic Polymer Beads for Solid-Supported Proline-Derived Organocatalysts," Organic Letters, 2009, vol. 11, No. 14, pp. 2968-2971.

Gruttadauria et al., "Hydrophobically Directed Aldol Reactions: Polystyrene-Supported L-Proline as a Recyclable Catalyst for Direct Asymmetric Aldol Reactions in the Presence of Water," Eur. J. Org. Chem., 2007, pp. 4688-4698.

Kristensen et al., "A General Approach for Preparation of Polymer-Supported Chiral Organocatalysts via Acrylic Copolymerization," J. Org. Chem., 2010, vol. 75, No. 5, pp. 1620-1629.

Sep. 2, 2014 International Search Report issued in International Patent Application No. PCT/JP2014/064770.

Sep. 2, 2014 Written Opinon issued in International Patent Application No. PCT/JP2014/064770.

*Primary Examiner* — Sikarl Witherspoon
(74) *Attorney, Agent, or Firm* — Oliff PLC

(57) ABSTRACT

An optically active compound production method using a column reactor, a column for column reactor is charged with asymmetric catalyst particles to produce the column reactor, and reaction compound is introduced into column reactor to bring reaction compound into contact with asymmetric catalyst particles, whereby reaction compound is converted to optically active compound. Asymmetric catalyst particles are preferably resin particles that are prepared from a monomer composition containing a proline derivative monomer having unsaturated bond and radical polymerization initiator and serve as catalyst for enamine mechanism reaction. Asymmetric catalyst particles are preferably resin particles prepared by micro-channel method including injecting monomer composition into continuous phase to thereby form droplets of monomer composition in continuous phase and then heating droplets to cause proline derivative monomer having an unsaturated bond to undergo radical polymerization.

18 Claims, 1 Drawing Sheet

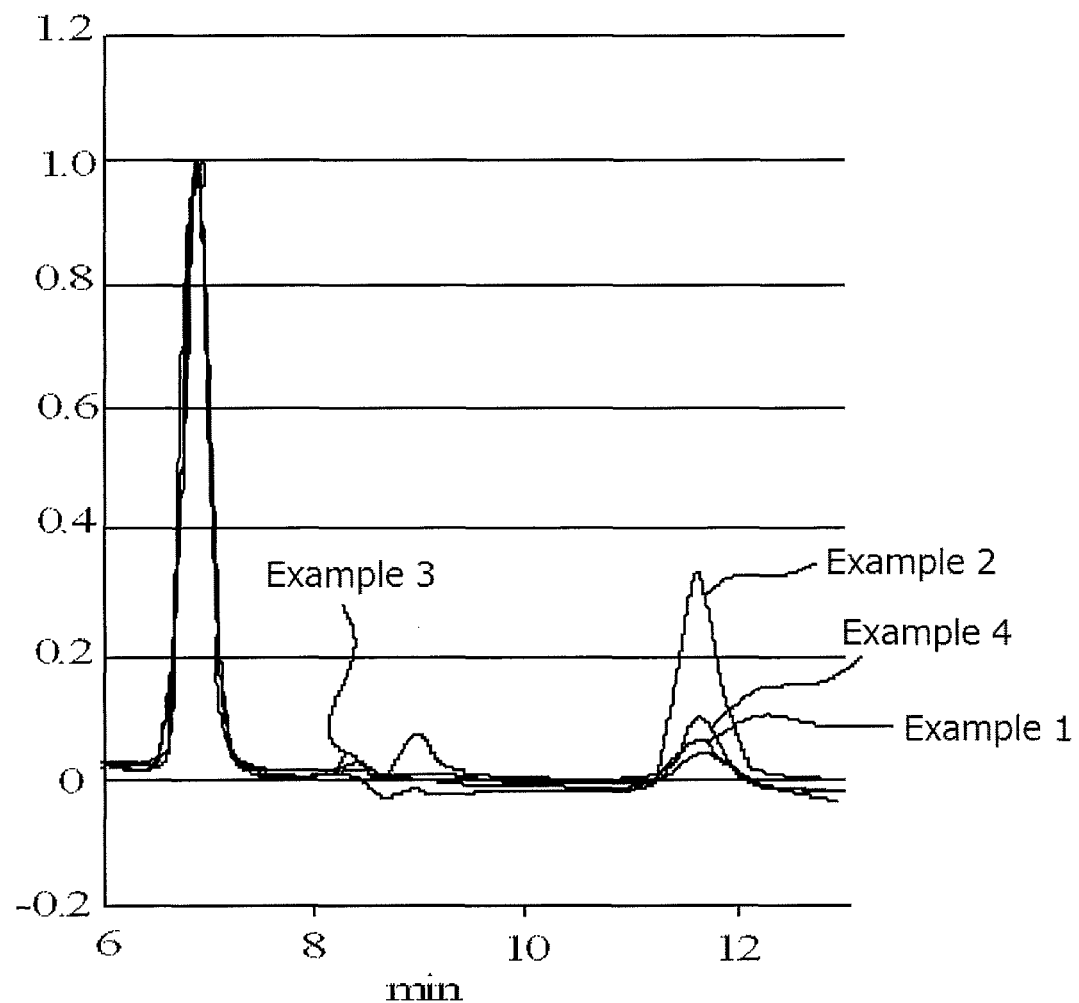

METHOD OF PRODUCING OPTICALLY ACTIVE COMPOUND

TECHNICAL FIELD

The present invention relates to a method of producing an optically active compound using a column reactor.

BACKGROUND ART

It has been found that proline and derivatives thereof act as organocatalysts for organic synthesis. Particularly, proline and derivatives thereof have advantages in that an optically active proline skeleton is easily available, no metal is used, and their use environment is not limited. Proline and derivatives thereof exhibit catalytic activity for reactions useful for synthesis of raw materials of pharmaceuticals etc., such as a Michael reaction, a Diels-Alder reaction, and reactions including an aldol reaction and a Mannich reaction that proceed through an enamine mechanism, with high yield and high enantioselectivity (Non-Patent Literature 1). As for such proline derivatives, solid-phase catalysts using the proline derivatives are also known. For example, it has been proposed to obtain an asymmetric aldol reaction product in a batch process in the following manner (Non-Patent Literature 2). Resin particles obtained by suspension polymerization of a monomer composition containing an acrylate derivative monomer having a proline structure in its molecule, an unsaturated compound such as styrene or divinylbenzene, and a radical polymerization initiator are used as solid-phase asymmetric catalyst particles. The resin particles are charged into a reaction container charged with a solution in which a carbonyl compound having an α hydrogen is dissolved, and then the reaction solution mixture is heated while being mixed uniformly to thereby obtain the asymmetric aldol reaction product.

CITATION LIST

Non-Patent Literature

Non-Patent Literature 1: ACC. Chem. Res. 2004, 37, 580-591
Non-Patent Literature 2: ORGANIC LETTERS, 2009, vol. 11, No. 14, 2968-2971

SUMMARY OF INVENTION

Technical Problem

However, for example, the asymmetric aldol reaction in the batch process using the asymmetric catalyst particles in Non-Patent Literature 2 has the following problems. The rate of stirring, reaction time, reaction temperature, etc. must be controlled separately according to the batch volume (scale) and batch shape, and a complicated separation operation is necessary to separate the reaction product from the catalyst.

An object of the present invention is to solve the foregoing problems in the prior art, specifically to produce an optically active compound using asymmetric catalyst particles serving as a solid-phase catalyst that can be easily applied to organic synthesis irrespective of the scale of production and can be separated from the reaction product without the need of a complicated separation operation.

Solution to Problem

The present inventors have found that the object of the present invention can be achieved by charging a column for a column reactor with asymmetric catalyst particles to produce the column reactor and then introducing a reaction compound(s) into the column reactor to bring the reaction compound(s) into contact with the asymmetric catalyst particles, whereby the reaction compound(s) is(are) converted to an optically active compound. Thus, the present invention has been completed.

Specifically, the present invention provides an optically active compound production method using a column reactor, the method including:
charging a column for the column reactor with asymmetric catalyst particles to produce the column reactor; and
introducing a reaction compound into the column reactor to bring the reaction compound into contact with the asymmetric catalyst particles, whereby the reaction compound is converted to an optically active compound.

The present invention also provides a column reactor comprising a column for the column reactor and asymmetric catalyst particles charged into the column, wherein the asymmetric catalyst particles are resin particles serving as a catalyst for a reaction that proceeds through an enamine mechanism (for example, an aldol reaction), and the resin particles are prepared from a monomer composition containing a proline derivative monomer having an unsaturated bond and a radical polymerization initiator.

The present invention further provides a column reactor production method comprising charging a column for a column reactor with asymmetric catalyst particles, wherein the asymmetric catalyst particles used are resin particles serving as a catalyst for a reaction that proceeds through an enamine mechanism, and the resin particles are prepared from a monomer composition containing a proline derivative monomer having an unsaturated bond and a radical polymerization initiator.

Advantageous Effects of Invention

In the optically active compound production method according to the present invention, the reaction compound(s) is(are) introduced into the column reactor charged with the asymmetric catalyst particles serving as the solid-phase catalyst to bring the reaction compound(s) into contact with the asymmetric catalyst particles, whereby the reaction compound(s) is(are) converted to the optically active compound. Therefore, the method can be easily applied to organic synthesis irrespective of the scale of the reaction. In addition, the optically active compound produced can be separated from the asymmetric catalyst particles without the need of a complicated separation operation.

BRIEF DESCRIPTION OF DRAWING(S)

FIG. 1 is an HPLC (high-performance liquid chromatography) chart of products in Examples 1 to 4.

DESCRIPTION OF EMBODIMENTS

The optically active compound production method of the present invention using a column reactor includes the following steps (a) and (b). These steps will next be described one by one.

<Step (a)>
First, a column for the column reactor is charged with asymmetric catalyst particles described later to prepare the column reactor. Examples of the column for the column reactor include glass columns, ceramic columns such as an alumina column, and metal columns such as a stainless steel column. A column for HPLC may be diverted to the column for the column reactor. Generally, an inlet for introducing a reaction solution is provided at one end of the column, and an outlet for discharging the reaction solution is provided at the other end.

From the viewpoint of handleability and the effects of the present invention, such a column has an inner diameter of 4.6 to 200 mm and a length of 10 to 10,000 mm.

To charge the asymmetric catalyst particles into the column, any known charging method can be used. For example, from the viewpoint of obtaining the effects of the present invention, the asymmetric catalyst particles are dispersed in a solvent such as ethanol, and the obtained dispersion is charged into the column at a flow rate of 0.1 to 500 mL/minute such that the maximum pressure is 10 to 200 MPa.

When the particle diameter of the asymmetric catalyst particles is small, the surface area of the asymmetric catalyst particles per unit mass becomes large, and the reaction field increases, so that the frequency of contact between a reaction compound and the asymmetric catalyst particles can be increased. When the particle diameter is large, a liquid can be easily injected into the column reactor. Therefore, the particle diameter is preferably 0.5 to 50 μm and more preferably 1 to 10 μm as measured by a flow type particle image analysis method.

<Step (b)>

Next, the reaction compound is introduced into the column reactor to bring the reaction compound into contact with the asymmetric catalyst particles, whereby the reaction compound is converted to an optically active compound. In this case, a reaction solution prepared by dissolving the reaction compound in a solvent may be injected into the column reactor using, for example, an HPLC system according to a routine procedure. A solvent used for the injection may be appropriately selected according to the types of the reaction compound etc. For example, from the viewpoint of obtaining the effects of the invention, a solvent mixture of water and acetonitrile (preferably 100:0 to 20:80 (% by volume)) may be used. The pressure of the injection is preferably 10 to 200 MPa, and the flow rate is preferably 0.1 to 500 mL/minute. The injection time is preferably 0.5 to 250 hours.

The optically active compound produced is discharged together with the solvent from the outlet of the column reactor. Therefore, it is preferable to collect a prescribed amount of the optically active compound at a prescribed time. If necessary, the aliquot is extracted with an organic solvent such as ethyl acetate, and the extract is concentrated. For example, from the viewpoint of obtaining the effects of the invention, the concentrate may be analyzed by HPLC using a solvent mixture such as hexane:isopropyl alcohol (99.9:0.1 to 70:30 (% by volume)) under the condition of a flow rate of 0.1 to 5 mL/minute to determine the rate of the reaction of the optically active compound. In the results of the analysis, the enantiomeric excess in the optically active compound production method of the present invention may be preferably 50 to 100% e.e. or more.

The reaction compound is selected according to, for example, a reaction catalyzed by the asymmetric catalyst particles. For example, when the asymmetric catalyst particles serve as a catalyst for the aldol reaction, the reaction compound contains a carbonyl compound having an α hydrogen and an aldehyde or a ketone. The aldehyde or ketone itself may be a carbonyl compound having an α hydrogen. The aldehyde or ketone to be reacted with the carbonyl compound having an α hydrogen may have no α hydrogen.

Examples of the aldehyde usable in the present invention may include: acyclic aldehydes such as ethanal, propanal, butyral, pentanal (valeraldehyde), and hexanal; alicyclic aldehydes such as cyclohexylcarboaldehyde; and aromatic aldehydes such as benzaldehyde, 4-nitrobenzaldehyde, 3-nitrobenzaldehyde, and 4-trifluoromethylbenzaldehyde. Examples of the ketones may include: acyclic ketones such as acetone, methyl ethyl ketone, diethyl ketone, methyl butyl ketone, and hydroxyacetone; and alicyclic ketones such as cyclopentanone and cyclohexanone.

As for the reaction compounds for the aldol reaction, when cyclohexanone is selected as the carbonyl compound having an α hydrogen and 4-nitrobenzaldehyde is selected as the aldehyde to be reacted with the carbonyl compound, 2-(hydroxy(4-nitrophenyl)methyl)cyclohexan-1-one can be obtained as the optically active compound. This compound has two asymmetric carbon atoms in its molecule. Therefore, this compound has four isomers shown below (Anti-1, Anti-2, and Syn (two types)). The ratio of these isomers produced can be controlled by selecting the type of the asymmetric catalyst particles.

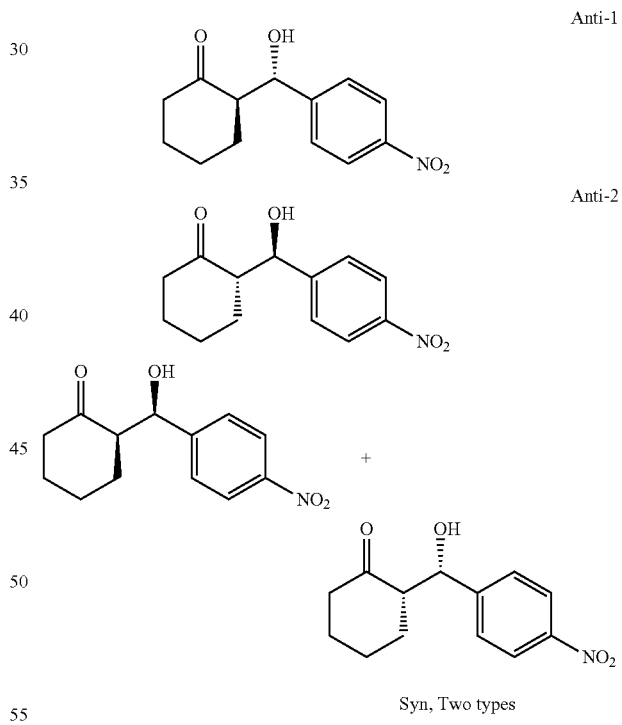

Similarly, when cyclohexanone and 3-nitrobenzaldehyde are selected, 2-(hydroxy(3-nitrophenyl)methyl)cyclohexan-1-one can be obtained as the optically active compound. When cyclohexanone and 4-trifluoromethylbenzaldehyde are selected, 2-(hydroxy(4-trifluoromethylphenyl)methyl)cyclohexan-1-one can be obtained as the optically active compound. Each of these compounds has four isomers (Anti-1, Anti-2, Syn (two types)). The ratio of these isomers produced can be controlled by selecting the type of the asymmetric catalyst particles.

When the asymmetric catalyst particles serve as a catalyst for the Mannich reaction, the reaction compound contains a carbonyl compound having an α hydrogen (such as an aldehyde or a ketone), a carbonyl compound having no α hydrogen (such as formaldehyde), and a primary or secondary amine compound. The optically active compound obtained from these compounds is a β-aminocarbonyl compound.

In the production method of the present invention, the optically active compound generated can be subjected to optical resolution in the column reactor by increasing one or both of the column length and the column diameter or changing the type of the developing solvent. Specifically, by increasing one or both of the column length and the column diameter, the amount of the catalyst used for optical resolution increases, and the frequency of interaction between the product and the catalyst thereby increases, so that the reaction product can be subjected to optical resolution and the rate of the reaction can be improved. By changing the solvent used to dissolve the reaction compounds to a different developing solvent, the interaction among the developing solvent, the product, and the catalyst is changed. In this case, the retention times of the optical isomers may become different from each other, so that the reaction product can be subjected to optical resolution.

(Asymmetric Catalyst Particles)

Examples of the asymmetric catalyst particles may include particles obtained by suspension polymerization of a monomer composition containing a monomer having a chiral source (such as BINAP (2,2'-bis(diphenylphosphino)-1,1'-binaphthyl)) using a known method and particles of a porous polymer or a porous ceramic which holds an organic compound serving as a chiral source (such as BINAP (2,2'-bis(diphenylphosphino)-1,1'-binaphthyl)) in its pore portions. Among them, preferred asymmetric catalyst particles are resin particles that are prepared by common suspension polymerization of a monomer composition containing a proline derivative monomer having an unsaturated bond and a radical polymerization initiator and serve as a catalyst for the aldol reaction or the Mannich reaction. Particularly preferred asymmetric catalyst particles are catalyst particles prepared by a micro-channel method in which the above-described monomer composition is injected into a continuous phase to form droplets of the monomer composition in the continuous phase and then the droplets are heated to cause the proline derivative monomer having an unsaturated bond to undergo radical polymerization. The micro-channel method will be described later.

The above monomer composition may further contain a monounsaturated or polyunsaturated compound monomer as needed. The effect obtained when a monounsaturated compound monomer is contained is that the monomer composition is reduced in viscosity. The effect obtained when a polyunsaturated compound monomer is contained is that the particles are increased in hardness.

The proline derivative monomer having an unsaturated bond that constitutes the monomer composition has a proline structure (any of structural formulas (A) to (D) below) that serves as a chiral source even after radical polymerization. The proline derivative monomer undergoes radical polymerization and forms part of a resin matrix in the catalyst particles. Examples of such a proline derivative monomer having an unsaturated bond include the following monomers.

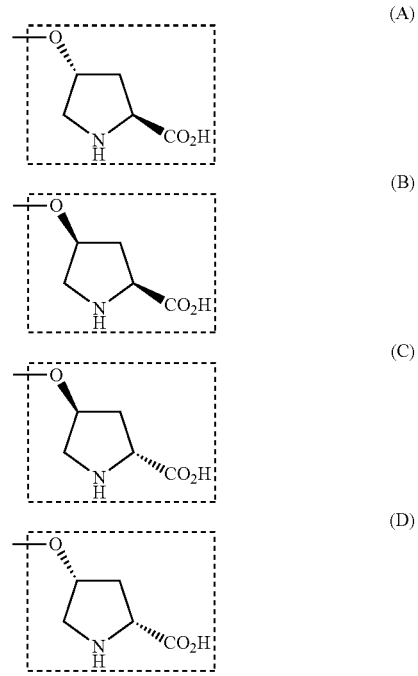

O-acryloyl-trans-4-hydroxy-L-proline
O-acryloyl-cis-4-hydroxy-L-proline
O-methacryloyl-trans-4-hydroxy-L-proline
O-methacryloyl-cis-4-hydroxy-L-proline
O-(2-methacryloyloxyethylsuccinoyl)-trans-4-hydroxy-L-proline
O-(2-methacryloyloxyethylsuccinoyl)-cis-4-hydroxy-L-proline
N-tert-butyloxycarbonyl-O-acryloyl-trans-4-hydroxy-L-proline
N-tert-butyloxycarbonyl-O-acryloyl-cis-4-hydroxy-L-proline
N-tert-butyloxycarbonyl-O-methacryloyl-trans-4-hydroxy-L-proline
N-tert-butyloxycarbonyl-O-methacryloyl-cis-4-hydroxy-L-proline
N-tert-butyloxycarbonyl-O-(2-methacryloyloxyethylsuccinoyl)-trans-4-hydroxy-L-proline
N-tert-butyloxycarbonyl-O-(2-methacryloyloxyethylsuccinoyl)-cis-4-hydroxy-L-proline
O-acryloyl-trans-4-hydroxy-D-proline
O-acryloyl-cis-4-hydroxy-D-proline
O-methacryloyl-trans-4-hydroxy-D-proline
O-methacryloyl-cis-4-hydroxy-D-proline
O-(2-methacryloyloxyethylsuccinoyl)-trans-4-hydroxy-D-proline
O-(2-methacryloyloxyethylsuccinoyl)-cis-4-hydroxy-D-proline
N-tert-butyloxycarbonyl-O-acryloyl-trans-4-hydroxy-D-proline
N-tert-butyloxycarbonyl-O-acryloyl-cis-4-hydroxy-D-proline
N-tert-butyloxycarbonyl-O-methacryloyl-trans-4-hydroxy-D-proline
N-tert-butyloxycarbonyl-O-methacryloyl-cis-4-hydroxy-D-proline
N-tert-butyloxycarbonyl-O-(2-methacryloyloxyethylsuccinoyl)-trans-4-hydroxy-D-proline N-tert-butyloxycarbonyl-O-(2-methacryloyloxyethylsuccinoyl)-cis-4-hydroxy-D-proline N-tert-butyloxycarbonyl-O-(4-vinylbenzyl)-trans-4-hydroxy-L-proline N-tert-butyloxycarbonyl-O-(4-vinylbenzyl)-cis-4-hydroxy-L-proline N-tert-butyloxycarbonyl-O-(4-vinylbenzyl)-trans-4-hydroxy-D-proline N-tert-butyloxycarbonyl-O-(4-vinylbenzyl)-cis-4-hydroxy-D-proline Of these, N-tert-butyloxycarbonyl-O-(2-methacryloyloxyethylsuccinoyl)-trans-4-hydroxy-L-proline, N-tert-butyloxycarbonyl-O-(2-methacryloyloxyethylsuccinoyl)-cis-4-hydroxy-D-proline, N-tert-butyloxycarbonyl-O-(4-vinylbenzyl)-trans-4-hydroxy-L-proline, and O-(2-methacryloyloxyethylsuccinoyl)-trans-4-hydroxy-L-proline can be used preferably from the viewpoint of availability of raw materials and the ease of synthesis. These compounds can be prepared with reference to Non-Patent Literatures 1 and 2 described above, J. Org. Chem., 2010, 75(5), pp 1620-1629, Eur. J. Org. Chem., 2007, pp 4688-4698, etc.

The monomer composition may contain, in addition to the proline derivative monomer having an unsaturated bond, a monounsaturated compound monomer or a polyunsaturated compound monomer as needed. The amount of the monounsaturated or polyunsaturated compound monomer added is preferably 100 to 10,000 parts by mass relative to 100 parts by mass of the proline derivative monomer having an unsaturated bond and more preferably 300 to 1,900 parts by mass.

Examples of the monounsaturated compound monomer may include olefins, monovinyl aromatics, and monofunctional (meth)acrylates (here, (meth)acrylates include acrylates and methacrylates).

Examples of the olefins may include ethylene, propylene, butene, and long-chain α-olefins. Examples of the monovinyl aromatics may include: styrene; nucleus alkyl-substituted monovinyl aromatic compounds such as methylstyrene and ethylstyrene; α-alkyl-substituted monovinyl aromatic compounds such as α-methylstyrene; β-alkyl-substituted styrenes; alkoxy-substituted styrenes; indene derivatives; and acenaphthylene derivatives.

Examples of the monofunctional (meth)acrylates may include methyl (meth)acrylate, ethyl (meth)acrylate, n-propyl (meth)acrylate, i-propyl (meth)acrylate, n-butyl (meth)acrylate, i-butyl (meth)acrylate, t-butyl (meth)acrylate, 2-methylbutyl (meth)acrylate, n-pentyl (meth)acrylate, n-hexyl (meth)acrylate, n-heptyl (meth)acrylate, 2-methylhexyl (meth)acrylate, 2-ethylhexyl (meth)acrylate, 2-butylhexyl (meth)acrylate, isooctyl (meth)acrylate, isopentyl (meth)acrylate, isononyl (meth)acrylate, isodecyl (meth)acrylate, cyclohexyl (meth)acrylate, benzyl (meth)acrylate, phenoxy (meth)acrylate, n-nonyl (meth)acrylate, n-decyl (meth)acrylate, lauryl (meth)acrylate, hexadecyl (meth)acrylate, and stearyl (meth)acrylate.

Examples of the polyunsaturated compound monomer may include polyvalent olefins, polyvalent vinyl aromatics, and polyfunctional (meth)acrylates.

Examples of the polyvalent olefins may include isoprene, 1,5-hexadiene, and 1,5-cyclooctadiene.

Examples of the polyvalent vinyl aromatics may include: divinyl aromatics such as m-divinylbenzene, p-divinylbenzene, 1,2-diisopropenylbenzene, 1,3-diisopropenylbenzene, 1,4-diisopropenylbenzene, 1,3-divinylnaphthalene, 1,8-divinylnaphthalene, 1,4-divinylnaphthalene, 1,5-divinylnaphthalene, 2,3-divinylnaphthalene, 2,7-divinylnaphthalene, 2,6-divinylnaphthalene, 4,4'-divinylbiphenyl, 4,3'-divinylbiphenyl, 4,2'-divinylbiphenyl, 3,2'-divinylbiphenyl, 3,3'-divinylbiphenyl, 2,2'-divinylbiphenyl, 2,4-divinylbiphenyl, 1,2-divinyl-3,4-dimethylbenzene, 1,3-divinyl-4,5,8-tributylnaphthalene, and 2,2'-divinyl-4-ethyl-4'-propylbiphenyl; and trivinyl aromatics (such as 1,2,4-trivinylbenzene, 1,3,5-trivinylbenzene, 1,2,4-triisopropenylbenzene, 1,3,5-triisopropenylbenzene, 1,3,5-trivinylnaphthalene, and 3,5,4'-trivinylbiphenyl.

Examples of the polyfunctional (meth)acrylates may include: bifunctional (meth)acrylates such as bisphenol F EO-modified di(meth)acrylate, bisphenol A EO-modified di(meth)acrylate, polypropylene glycol di(meth)acrylate, polyethylene glycol (meth)acrylate, tricyclodecanedimethylol di(meth)acrylate, and dicyclopentadiene (meth)acrylate; trifunctional (meth)acrylates such as trimethylolpropane tri(meth)acrylate, trimethylolpropane PO-modified (meth)acrylate, and isocyanuric acid EO-modified tri(meth)acrylate; and tetra- and higher functional (meth)acrylates such as dipentaerythritol penta(meth)acrylate, pentaerythritol hexa(meth)acrylate, pentaerythritol tetra(meth)acrylate, and ditrimethylolpropane tetraacrylate. In addition, polyfunctional urethane (meth)acrylates can be used. Specific examples thereof may include: M1100, M1200, M1210, and M1600 (Toagosei Co., Ltd.); and AH-600 and AT-600 (Kyoeisha Chemical Co., Ltd.).

Among the monounsaturated and polyunsaturated compound monomers described above, divinylbenzene can be used preferably in terms of its acid-base resistance, solvent resistance, particle hardness, and viscosity.

The radical polymerization initiator constituting the monomer composition is a compound that generates radicals under heating, and examples thereof may include azo-based compounds and organic peroxides. Examples of the azo-based compounds may include azobisalkanonitrile. Examples of the organic peroxides may include diacyl peroxide, peroxydicarbonate, peroxyesters, peroxyketals, dialkyl peroxides, and hydroperoxides. One important index used to select a radical polymerization initiator from the above compounds is "decomposition temperature." The low-temperature fast curability of the monomer composition tends to be improved as the decomposition temperature decreases. In the present description, the decomposition temperature of the radical polymerization initiator specifically means 10 hour half-life temperature.

Specific examples of the radical polymerization initiator usable in the present invention may include azobisisobutyronitrile (decomposition temperature: 65° C.), diisobutyryl peroxide (decomposition temperature: 32.7° C.), 1,1,3,3-tetramethylbutylperoxy-2-ethylhexanoate (decomposition temperature: 65.3° C.), dilauroyl peroxide (decomposition temperature: 61.6° C.), di(3,5,5-trimethylhexanoyl)peroxide (decomposition temperature: 59.4° C.), t-butyl peroxypivalate (decomposition temperature: 54.6° C.), t-hexyl peroxypivalate (decomposition temperature: 53.2° C.), t-butyl peroxyneoheptanoate (decomposition temperature: 50.6° C.) t-butyl peroxyneodecanoate (decomposition temperature: 40.7° C.), t-hexyl peroxyneodecanoate (decomposition temperature: 44.5° C.), di(2-ethylhexyl)peroxydicarbonate (decomposition temperature: 43.6° C.), di(4-t-butylcyclohexyl)peroxydicarbonate (decomposition temperature: 40.8° C.), 1,1,3,3-tetramethylbutyl peroxyneodecanoate (decomposition temperature: 40.7° C.), di-sec-butyl peroxydicarbonate (decomposition temperature: 40.5° C.), di-n-propyl peroxydicarbonate (decomposition temperature: 40.3° C.), cumyl peroxyneodecanoate (decomposition temperature: 36.5° C.), di(4-methylbenzoyl)peroxide (decomposition temperature: 70.6° C.), di(3-methylbenzoyl)peroxide (decomposition temperature: 73.1° C.), dibenzoyl peroxide (decomposition temperature: 73.6° C.), 1,1-di(t-butylperoxy)-2-methylcyclohexane (decomposition temperature: 83.2° C.), 1,1-di(t-hexylperoxy)cyclohexane (decomposition temperature: 87.1° C.), 1,1-di(t-butylperoxy) cyclohexane (decomposition temperature: 90.7° C.), t-hexyl peroxybenzoate (decomposition temperature: 99.4° C.), t-butyl peroxybenzoate (decomposition temperature: 104.7° C.), methyl ethyl ketone peroxide (decomposition temperature: 15 to 35° C.), cyclohexanone peroxide, methylcyclohexanone peroxide, t-butyl hydroperoxide, t-amyl hydroperoxide (decomposition temperature: 258° C.), t-hexyl hydroperoxide (decomposition temperature: 116.4° C.), t-octyl hydroperoxide (decomposition temperature: 150° C.), 2,5-dimethyl-2,5-dihydroperoxyhexane (decomposition temperature: 118° C.), cumene hydroperoxide (decomposition temperature: 157.9° C.), diisopropyl benzene monohydroperoxide, diisopropyl benzene dihydroperoxide (decomposition temperature: unknown), and p-menthane hydroperoxide (decomposition temperature: 128.0° C.). A combination of two or more types of these radical polymerization initiators may be used. When a peroxide having a phenyl ring and having high decomposition temperature is used, the cohesion of the polymer generated can be improved.

To achieve sufficient curing and to avoid a reduction in the degree of polymerization to thereby prevent a reduction in mechanical strength, the amount of the radical polymerization initiator added to the monomer composition is preferably 1 to 40 parts by mass and more preferably 1 to 20 parts by mass relative to 100 parts by mass of the total of the proline derivative monomer having an unsaturated bond and the monounsaturated and polyunsaturated compound monomers added as needed.

If necessary, a non-polymerizable polymer, an organic filler, an inorganic filler, a pigment, etc. may be added to the monomer composition.

(Micro-Channel Method)

As described above, particularly preferred asymmetric catalyst particles are catalyst particles prepared by the micro-channel method. In this method, the above-described monomer composition is injected into a continuous phase to form droplets of the monomer composition in the continuous phase, and then the droplets are heated to cause the proline derivative monomer having an unsaturated bond to undergo radical polymerization. This micro-channel method includes the following steps (A) and (B). These steps will next be described one by one.

<Step (A)>

First, the monomer composition containing the proline derivative monomer having an unsaturated bond and the radical polymerization initiator is injected into the continuous phase from a micro channel to thereby form droplets of the monomer composition in the continuous phase. This state is generally a liquid-liquid emulsion. To inject the monomer composition into the continuous phase from the micro-channel, any known micro-reactor provided with a micro-channel (see, for example, Japanese Patent Nos. 2975943, 2981547, and 3616909) can be used. A commercially available micro-reactor may be used. No particular limitation is imposed on the micro-channel applicable to these micro-reactors. For example, a micro-syringe, a micro-channel chip produced by forming grooves on a glass substrate by etching, etc. can be used.

The size of the droplets of the monomer composition can be controlled by appropriately selecting the groove width, groove depth, groove length, groove wall material of the micro-channel, injection pressure, the type of a dispersion medium constituting the continuous phase, a dispersant, etc. The size of the droplets is generally 1 to 100 μm. This size is the final size of the asymmetric catalyst particles.

The continuous phase functions as a dispersion medium of the droplets of the monomer composition and is generally prepared by dissolving a dispersant in water such as ion exchanged water. The dispersant can be appropriately selected from known cationic, anionic, nonionic, and amphoteric surfactants according to the types of the components of the monomer composition, the diameter of the droplets, etc.

Examples of the anionic surfactants may include soap (fatty acid sodium salts), monoalkyl sulfates, alkylpolyoxyethylene sulfates, alkylbenzene sulfonates, and monoalkyl phosphates. Examples of the cationic surfactants may include alkyltrimethyl ammonium salts, dialkyldimethyl ammonium salts, and alkylbenzyldimethyl ammonium salts. Examples of the amphoteric surfactants may include alkyldimethylamine oxides and alkylcarboxy betaines. Examples of the nonionic surfactants may include polyoxyethylenealkyl ethers, sorbitan fatty acid esters, alkyl polyglucosides, fatty acid diethanol amides, and alkylmonoglyceryl ethers.

The amount of the surfactant contained in the continuous phase is generally 0.01 to 10% by weight and preferably 0.05 to 5% by weight.

If necessary, a stabilizer may be added to the continuous phase in order to stabilize the dispersion state of the droplets of the monomer composition and its polymerization product, i.e., the asymmetric catalyst particles. For example, the continuous phase may contain any of water-soluble macromolecules such as polyvinyl alcohol, polyvinylpyrrolidone, carboxymethyl cellulose, hydroxymethyl cellulose, starch, and gelatin, poorly water-soluble inorganic salts such as tricalcium phosphate, etc.

In addition, the continuous phase may contain known additives such as a chelating agent (glycine, alanine, ethylenediaminetetraacetic acid sodium salt, etc.), a pH buffer (sodium tripolyphosphate, potassium tetrapolyphosphate, etc.), a sensitizer, and a viscosity modifier.

<Step (B)>

Next, the droplets of the monomer composition in the continuous phase are heated to cause the proline derivative monomer having an unsaturated bond to undergo radical polymerization. The droplets of the monomer composition may be heated by irradiation with microwaves. The heating temperature of the droplets of the monomer composition can be controlled by changing, for example, the output energy of the microwave irradiation, and the level of the mechanical properties of the asymmetric catalyst particles can thereby be controlled. The reason of this is as follows. During heating by irradiation with microwaves, it has been confirmed that polymerization and also depolymerization occur. However, as the heating temperature increases, polymerization becomes dominant over depolymerization, so that the mechanical properties of the polymer, for example, compressive strength (hardness of the particles), can be changed (in other words, can be controlled) without changing the chemical composition of the monomer composition. The microwave irradiation apparatus used may be a commercially available apparatus.

The asymmetric catalyst particles obtained by the micro-channel method are generally suspended in the continuous phase and can be isolated by, for example, filtration or centrifugation. The average particle diameter, 50% particle diameter, and standard deviation of the asymmetric catalyst particles can be measured using a commercially available particle diameter measurement apparatus. From the viewpoint of obtaining the effects of the invention, a preferred average particle diameter is 0.5 to 50 µm, and a preferred 50% particle diameter is 0.5 to 50 µm. A preferred standard deviation is $5 \times 10^{-4}$ to 10 µm and a preferred CV value (=standard deviation/average particle diameter×100) is 0.1 to 20%.

<Column Reactor>

As described above, the column reactor is prepared by charging a column for the column reactor with the asymmetric catalyst particles. The column reactor particularly preferably applicable to the "optically active compound production method" of the present invention uses, as the asymmetric catalyst particles, resin particles prepared from the monomer composition containing the proline derivative monomer having an unsaturated bond and the radical polymerization initiator. These resin particles serve as a catalyst for an enamine mechanism reaction such as the aldol reaction or the Mannich reaction. Particularly, the column reactor uses asymmetric catalyst particles prepared according to the micro-channel method. Specifically, the monomer composition is injected into a continuous phase to form droplets of the monomer composition in the continuous phase, and then the droplets are heated to cause the proline derivative monomer having an unsaturated bond to undergo radical polymerization. Preferably, N-tert-butyloxycarbonyl-O-(2-methacryloyloxyethylsuccinoyl)-trans-4-hydroxy-L-proline, N-tert-butyloxycarbonyl-O-(2-methacryloyloxyethylsuccinoyl)-cis-4-hydroxy-D-proline, or N-tert-butyloxycarbonyl-O-(4-vinylbenzyl)-trans-4-hydroxy-L-proline can be used as the proline derivative monomer having an unsaturated bond. Preferably, the monomer composition further contains a monounsaturated or polyunsaturated compound monomer, preferably divinylbenzene. The above-described column reactor is also one aspect of the present invention, and a method of producing the column reactor is also one aspect of the present invention.

Specifically, the method of producing the column reactor is characterized in that the above-described column for the column reactor is charged with the above-described resin particles prepared from the monomer composition containing the proline derivative monomer having an unsaturated bond and the radical polymerization initiator. These resin particles are asymmetric catalyst particles serving as a catalyst for a reaction that proceeds through the enamine mechanism. Particularly, it is preferable to use asymmetric catalyst particles prepared according to the micro-channel method including injecting the monomer composition into a continuous phase to form droplets of the monomer composition in the continuous phase and then heating the droplets to cause the proline derivative monomer having an unsaturated bond to undergo radical polymerization.

EXAMPLE(S)

The present invention will next be described specifically by way of Examples.

Example 1

(Preparation of Asymmetric Catalyst Particles by Micro-Channel Method)

A monomer composition including 10 parts by mass of N-tert-butyloxycarbonyl-O-(2-methacryloyloxyethylsuccinoyl)-trans-4-hydroxy-L-proline synthesized with reference to Non-Patent Literature 1 or 2 or J. Org. Chem., 2010, 75(5), pp 1620-1629, 1 part by mass of dilauroyl peroxide (PEROYL L, NOF Corporation), 90 parts by mass of divinylbenzene, and 10 parts by mass of isooctane was prepared as a disperse phase. In addition, as a continuous phase, an aqueous solution (a continuous phase solution) produced by dissolving 1% by mass of a surfactant (SSL, Kao Corporation) in ion exchanged water was prepared.

The prepared disperse phase and continuous phase were applied to a micro-reactor (Eco Project Technologies Co., Ltd.) having a micro-channel (width: 5 µm, depth: 1 µm, length: 100 µm). Then the disperse phase was extruded into the continuous phase to form droplets of the monomer composition having an average particle diameter of 3 µm. While the obtained mixture was mixed, ion exchanged water and a surfactant (SSL, Kao Corporation) were added to prepare a slurry in which the concentration of the droplets of the monomer composition was 4% by mass and the concentration of the surfactant was 1% by mass.

The obtained slurry was heated and stirred at 90 to 100° C. for 7 hours, collected on a filter, and then dried in a vacuum to obtain asymmetric catalyst particles in which polymerization and deprotection had been completed. The particle diameter of the asymmetric catalyst particles was measured using a flow type particle image analyzer (FPIA-3000, Sysmex). The average particle diameter was 2.839 µm, the 50% particle diameter was 2.841 µm, the standard deviation was 0.12 µm, and the CV value was 4.23%.

(Preparation of Column Reactor)

A mixture prepared by mixing the obtained asymmetric catalyst particles with an equal mass of ethanol was subjected to ultrasonic dispersion treatment, and the obtained dispersion was charged into a stainless steel column (outer diameter: ¼ inches, inner diameter: 4.6 mm, length: 150 mm, Cat-No. 6010-11053, GL Sciences Inc.) at a flow rate of 1.0 mL/minute to thereby obtain a column reactor for producing an optically active compound. In this case, the maximum pressure applied was 30 MPa.

(Production of Optically Active Compound)

The interior of the obtained column reactor was replaced with a mobile phase (water:acetonitrile:cyclohexanone=83% by volume:15% by volume:2% by volume). A cyclohexanone solution of 4-nitrobenzaldehyde (Tokyo Chemical Industry Co., Ltd.) with its concentration adjusted to 2.9% by mass was injected into the above column reactor at a flow rate of 0.4 mL/minute and a pressure of 10.7 MPa and developed for 2 hours. The reaction solution discharged from the column reactor was extracted with ethyl acetate, and the extract was concentrated to obtain a mixture of isomers of 2-(hydroxy(4-nitrophenyl)methyl)cyclohexan-1-one. The mixture of isomers of 2-(hydroxy(4-nitrophenyl)methyl)cyclohexan-1-one was analyzed by HPLC (LC-20A, Shimadzu Corporation (column: CHIRALPAK AD-H, Daicel Corporation, mobile phase: hexane-isopropyl alcohol mixed solvent (85% by volume:15% by volume))), and the enantiomeric excess was found to be 77% e.e. The rate of the reaction based on aldehyde was 16%.

Example 2

2-(Hydroxy(4-nitrophenyl)methyl)cyclohexan-1-one was obtained in the same manner as in Example 1 except that, when the optically active compound was produced, the cyclohexanone solution of 4-nitrobenzaldehyde (Tokyo Chemical Industry Co., Ltd.) with its concentration adjusted to 2.9% by mass was injected at a flow rate of 0.1 mL/minute and a pressure of 2.7 MPa and developed for 5 hours. The obtained compound was analyzed by HPLC as in Example 1, and the enantiomeric excess was found to be 74% e.e. The rate of the reaction based on aldehyde was 50%.

Example 3

2-(Hydroxy(4-nitrophenyl)methyl)cyclohexan-1-one was obtained in the same manner as in Example 1 except that, when the optically active compound was produced, a cyclohexanone solution of 4-nitrobenzaldehyde (Tokyo Chemical Industry Co., Ltd.) with its concentration adjusted to 13.7% by mass was injected at a flow rate of 0.4 mL/minute and a pressure of 10.7 MPa and developed for 2 hours. The obtained compound was analyzed by HPLC as in Example 1, and the enantiomeric excess was found to be 50% e.e. The rate of the reaction based on aldehyde was 27%.

Example 4

2-(Hydroxy(4-nitrophenyl)methyl)cyclohexan-1-one was obtained in the same manner as in Example 1 except that, when the optically active compound was produced, a cyclohexanone solution of 4-nitrobenzaldehyde (Tokyo Chemical Industry Co., Ltd.) with its concentration adjusted to 13.7% by mass was injected at a flow rate of 0.2 mL/minute and a pressure of 5.3 MPa and developed for 4 hours. The obtained compound was analyzed by HPLC as in Example 1, and the enantiomeric excess was found to be 87% e.e. The rate of the reaction based on aldehyde was 28%.

Summary of Examples

TABLE 1 shows the reaction conditions in the column reactor, the relative intensities of the isomers (Anti-1, Anti-2, Syn (two types)) of the produced 2-(hydroxy(4-nitrophenyl)methyl)cyclohexan-1-one in an HPLC chart (see FIG. 1), the rate of the reaction, and the enantiomeric excess for each of Examples 1 to 4. The HPLC chart is shown in FIG. 1.

TABLE 1

|  |  |  | EXAMPLE | | | |
| --- | --- | --- | --- | --- | --- | --- |
|  |  |  | 1 | 2 | 3 | 4 |
| COLUMN REACTOR CONDITIONS | 4-NITROBENZALDEHYDE CONCENTRATION | [% by mass] | 2.9 | 2.9 | 13.7 | 13.7 |
|  | FLOW RATE | [ml/min] | 0.4 | 0.1 | 0.4 | 0.2 |
|  | PRESSURE | [Mpa] | 10.7 | 2.7 | 10.7 | 5.3 |
|  | TIME | [hr] | 2 | 5 | 2 | 4 |
| HPLC RESULTS | Anti-1 | 9.09 min | 15293 | 56380 | 25769 | 9722 |
|  | Anti-2 | 11.83 min | 121272 | 385412 | 77160 | 143608 |
|  | RATE OF REACTION | [%] | 16 | 50 | 27 | 28 |
|  | ENANTIOMERIC EXCESS | [% e.e.] | 77 | 74 | 50 | 87 |

As can be seen from the results in Examples 1 to 4, by introducing the reaction compounds into the column reactor charged with the asymmetric catalyst particles to bring the reaction compounds into contact with the asymmetric catalyst particles, the reaction compounds can be converted to the optically active compound. By decreasing the flow rate, the rate of the reaction increases. In this case, the enantiomeric excess can also increase.

Example 5

(Preparation of Asymmetric Catalyst Particles by Micro-Channel Method)

A monomer composition including 10 parts by mass of N-tert-butyloxycarbonyl-O-(2-methacryloyloxyethylsuccinoyl)-cis-4-hydroxy-D-proline synthesized with reference to Non-Patent Literature 1 or 2 or J. Org. Chem., 2010, 75(5), pp 1620-1629, 1 part by mass of dilauroyl peroxide (PEROYL L, NOF Corporation), 90 parts by mass of divinylbenzene, and 30 parts by mass of isooctane was prepared as a disperse phase. In addition, as a continuous phase, an aqueous solution (a continuous phase solution) produced by dissolving 1% by mass of a surfactant (SSL, Kao Corporation) in ion exchanged water was prepared.

The prepared disperse phase and continuous phase were applied to a micro-reactor (Eco Project Technologies Co., Ltd.) having a micro-channel (width: 5 μm, depth: 1 μm, length: 100 μm). Then the disperse phase was extruded into the continuous phase to form droplets of the monomer composition having an average particle diameter of 3 μm. While the obtained mixture was mixed, ion exchanged water and a surfactant (SSL, Kao Corporation) were added to prepare a slurry in which the concentration of the droplets of the monomer composition was 4% by mass and the concentration of the surfactant was 1% by mass.

The obtained slurry was heated and stirred at 90 to 100° C. for 7 hours, collected on a filter, and then dried in a vacuum to obtain asymmetric catalyst particles in which polymerization and deprotection had been completed. The particle diameter of the asymmetric catalyst particles was measured using a flow type particle image analyzer (FPIA-3000, Sysmex). The average particle diameter was 2.839 μm, the 50% particle diameter was 2.834 μm, the standard deviation was 0.159 μm, and the CV value was 5.63%.

(Preparation of Column Reactor)

A mixture prepared by mixing the obtained asymmetric catalyst particles with a two-fold amount by mass of ethanol was subjected to ultrasonic dispersion treatment, and the obtained dispersion was charged into a stainless steel column (outer diameter: ¼ inches, inner diameter: 4.6 mm, length: 150 mm, Cat-No. 6010-11053, GL Sciences Inc.) at a flow rate of 1.0 mL/minutes to thereby obtain a column reactor for producing an optically active compound. In this case, the maximum pressure applied was 27.6 MPa.

(Production of Optically Active Compound)

The interior of the obtained column reactor was replaced with a mobile phase (water:acetonitrile:cyclohexanone=74% by volume:24% by volume:2% by volume). A cyclohexanone solution of 4-nitrobenzaldehyde (Tokyo Chemical Industry Co., Ltd.) with its concentration adjusted to 13.7% by mass was injected into the above column reactor at a flow rate of 0.2 mL/minute and a pressure of 4.7 MPa and developed for 5 hours. The reaction solution discharged from the column reactor was extracted with ethyl acetate, and the extract was concentrated to obtain a mixture of isomers of 2-(hydroxy(4-nitrophenyl)methyl)cyclohexan-1-one. The mixture of isomers of 2-(hydroxy(4-nitrophenyl)methyl)cyclohexan-1-one was analyzed by HPLC (LC-20A, Shimadzu Corporation (column: CHIRALPAK AD-H, Daicel Corporation, mobile phase: hexane-isopropyl alcohol mixed solvent (85% by volume:15% by volume))), and the enantiomeric excess was found to be 96% e.e. The rate of the reaction based on aldehyde was 7%.

Example 6

2-(Hydroxy(4-nitrophenyl)methyl)cyclohexan-1-one was obtained in the same manner as in Example 5 except that, when the optically active compound was produced, the cyclohexanone solution of 4-nitrobenzaldehyde (Tokyo Chemical Industry Co., Ltd.) with its concentration adjusted to 13.7% by mass was injected at a flow rate of 0.1 mL/minute and a pressure of 2.5 MPa and developed for 12 hours. The obtained compound was analyzed by HPLC as in Example 1, and the enantiomeric excess was found to be 97% e.e. The rate of the reaction based on aldehyde was 13%.

Example 7

Asymmetric catalyst particles were obtained in the same manner as in Example 5 except that, when the asymmetric catalyst particles were produced, N-tert-butyloxycarbonyl-O-(4-vinylbenzyl)-trans-4-hydroxy-L-proline was used instead of N-tert-butyloxycarbonyl-O-(2-methacryloyloxy-ethylsuccinoyl)-trans-4-hydroxy-L-proline. The particle diameter of the asymmetric catalyst particles was measured using a flow type particle image analyzer (FPIA-3000, Sysmex). The average particle diameter was 2.764 µm, the 50% particle diameter was 2.739 µm, the standard deviation was 0.129 µm, and the CV value was 4.74%.

The obtained asymmetric catalyst particles were used to obtain a column reactor for producing an optically active compound in the same manner as in Example 5. In this case, the maximum pressure applied was 25.7 MPa.

2-(Hydroxy(4-nitrophenyl)methyl)cyclohexan-1-one was obtained in the same manner as in Example 5 except that, when the optically active compound was produced using the obtained column reactor, the cyclohexanone solution of 4-nitrobenzaldehyde (Tokyo Chemical Industry Co., Ltd.) with its concentration adjusted to 13.7% by mass was injected at a flow rate of 0.2 mL/minute and a pressure of 4.9 MPa and developed for 3.5 hours. The obtained compound was analyzed by HPLC as in Example 1, and the enantiomeric excess was found to be 97% e.e. The rate of the reaction based on aldehyde was 12%.

Example 8

2-(Hydroxy(4-nitrophenyl)methyl)cyclohexan-1-one was obtained in the same manner as in Example 7 except that, when the optically active compound was produced, the cyclohexanone solution of 4-nitrobenzaldehyde (Tokyo Chemical Industry Co., Ltd.) with its concentration adjusted to 13.7% by mass was injected at a flow rate of 0.1 mL/minute and a pressure of 2.4 MPa and developed for 8 hours. The obtained compound was analyzed by HPLC as in Example 1, and the enantiomeric excess was found to be 98% e.e. The rate of the reaction based on aldehyde was 22%.

Example 9

A column reactor for producing an optically active compound was obtained in the same manner as in Example 7 except that, when the column reactor was produced, a stainless steel column having an outer diameter of ⅜ inches, an inner diameter of 7.6 mm, and a length of 300 mm (Cat-No. 6010-11076, GL Sciences Inc.) was used. In this case, the maximum pressure applied was 17.4 MPa.

2-(Hydroxy(4-nitrophenyl)methyl)cyclohexan-1-one was obtained in the same manner as in Example 5 except that, when the optically active compound was produced using the obtained column reactor, the cyclohexanone solution of 4-nitrobenzaldehyde (Tokyo Chemical Industry Co., Ltd.) with its concentration adjusted to 13.7% by mass was injected at a flow rate of 0.2 mL/minute and a pressure of 2.8 MPa and developed for 24 hours. The obtained compound was analyzed by HPLC as in Example 1, and the enantiomeric excess was found to be 93% e.e. The rate of the reaction based on aldehyde was 43%.

Example 10

2-(Hydroxy(4-nitrophenyl)methyl)cyclohexan-1-one was obtained in the same manner as in Example 9 except that, when the optically active compound was produced, the cyclohexanone solution of 4-nitrobenzaldehyde (Tokyo Chemical Industry Co., Ltd.) with its concentration adjusted to 13.7% by mass was injected at a flow rate of 1.0 mL/minute and a pressure of 12.9 MPa and developed for 4 hours. The obtained compound was analyzed by HPLC as in Example 1, and the enantiomeric excess was found to be 96% e.e. The rate of the reaction based on aldehyde was 13%.

Example 11

2-(Hydroxy(3-nitrophenyl)methyl)cyclohexan-1-one was obtained in the same manner as in Example 9 except that, when the optically active compound was produced, a cyclohexanone solution of 3-nitrobenzaldehyde (Tokyo Chemical Industry Co., Ltd.) with its concentration adjusted to 13.7% by mass was injected instead of the cyclohexanone solution of 4-nitrobenzaldehyde (Tokyo Chemical Industry Co., Ltd.) with its concentration adjusted to 13.7% by mass at a flow rate of 1.0 mL/minute and a pressure of 13 MPa and was developed for 5 hours. The obtained compound was analyzed by HPLC as in Example 1 (however, a hexane-isopropyl alcohol mixed solvent of 90% by volume:10% by volume was used as the mobile phase), and the enantiomeric excess was found to be 92% e.e. The rate of the reaction based on aldehyde was 6%.

Example 12

2-(Hydroxy(4-trifluoromethylphenyl)methyl)cyclohexan-1-one was obtained in the same manner as in Example 9 except that, when the optically active compound was produced, a cyclohexanone solution of 4-trifluoromethylbenzaldehyde (Tokyo Chemical Industry Co., Ltd.) with its concentration adjusted to 13.7% by mass was injected instead of the cyclohexanone solution of 4-nitrobenzaldehyde (Tokyo Chemical Industry Co., Ltd.) with its concentration adjusted to 13.7% by mass at a flow rate of 1.0 mL/minute and a pressure of 13.7 MPa and developed for 5 hours. The obtained compound was analyzed by HPLC as in Example 1 (however, a hexane-isopropyl alcohol mixed solvent of 95% by volume:5% by volume was used as the mobile phase, and the column used was CHIRALPAK OD-H available from Daicel Corporation), and the enantiomeric excess was found to be 95% e.e. The rate of the reaction based on aldehyde was 24%.

TABLE 2 shows a list of the raw materials of asymmetric catalyst particles, the conditions for the preparation of the column reactor, the conditions for the production of the optically active compound (the reaction conditions in the column reactor), and the conditions and results of the analysis of the optically active compound for each of Examples 1 to 12.

TABLE 2

| | | | | EXAMPLE | | | | | |
|---|---|---|---|---|---|---|---|---|---|
| | | | | 1 | 2 | 3 | 4 | 5 | 6 |
| Asymmetric Catalyst Particles | Composition | N-tert-butyloxycarbonyl-o-(2-methacryloyloxyethylsuccinoyl)-trans-4-hydroxy-L-proline | [parts by mass] | 10 | ← | ← | ← | | |
| | | N-tert-butyloxycarbonyl-o-(2-methacryloyloxyethylsuccinoyl)-cis-4-hydroxy-D-proline | [parts by mass] | | | | | 10 | ← |
| | | N-tert-butyloxycarbonyl-o-(4-vinylbenzyl)-trans-4-hydroxy-L-proline | [parts by mass] | | | | | | |
| | | Divinylbenzene | [parts by mass] | 90 | ← | ← | ← | ← | ← |
| | | Isooctane | [parts by mass] | 10 | ← | ← | ← | 30 | ← |
| | | Dilauroyl Peroxide | [parts by mass] | 1 | ← | ← | ← | ← | ← |
| | Particle Diameter Analysis | Apparatus Used: FPIA-3000, Sysmex | Average Particle Diameter [μm] | 2.839 | ← | ← | ← | 2.839 | ← |
| | | | 50% Particle Diameter [μm] | 2.841 | ← | ← | ← | 2.834 | ← |
| | | | Standard Deviation [μm] | 0.12 | ← | ← | ← | 0.159 | ← |
| | | | CV Value [%] | 4.23 | ← | ← | ← | 5.63 | ← |
| Colum Reactor Preparation Conditions | Column Size | | Outer Diameter [inch] | ¼ | ← | ← | ← | ← | ← |
| | | | Inner Diameter [mm] | 4.6 | ← | ← | ← | ← | ← |
| | | | Length [mm] | 150 | ← | ← | ← | ← | ← |
| | Dispersion Medium | | Type | EtOH | ← | ← | ← | ← | ← |
| | Flow Rate | | [ml/min] | 1 | ← | ← | ← | ← | ← |
| | Maximum Pressure | | [Mpa] | 30 | ← | ← | ← | 27.6 | ← |
| Column Reactor Reaction Conditions | Substrate Concentration | 4-Nitrobenzaldehyde | [wt %] | 2.9 | 2.9 | 13.7 | ← | ← | ← |
| | | 3-Nitrobenzaldehyde | [wt %] | | | | | | |
| | | 4-Trifluorobenzaldehyde | [wt %] | | | | | | |
| | Mobile Phase Conditions | Water:Acetonitrile:Cyclohexanone | [Vol %] | 83:15:02 | ← | ← | ← | 74:24:02 | ← |
| | | Flow Rate | [ml/min] | 0.4 | 0.1 | 0.4 | 0.2 | 0.2 | 0.1 |
| | | Pressure | [Mpa] | 10.7 | 2.7 | 10.7 | 5.3 | 4.7 | 2.5 |
| | | Time | [hr] | 2 | 5 | 2 | 4 | 5 | 12 |
| Conditions for Analysis of Optically Active Compound | Analysis Target | 2-(Hydroxy(4-nitrophenyl)methyl)cyclohexan-1-one | Column Used for Analysis | AD-H | AD-H | AD-H | AD-H | AD-H | AD-H |
| | | 2-(Hydroxy(3-nitrophenyl)methyl)cyclohexan-1-one | | | | | | | |
| | | 2-(Hydroxy(4-trifluoromethylphenyl)methyl)cyclohexan-1-one | | | | | | | |
| | HPLC Conditions | Solvent (Hexane:Isopropyl Alcohol) | [Vol %] | 85:15 | 85:15 | 85:15 | 85:15 | 85:15 | 85:15 |
| | | Flow Rate | [ml/min] | 1 | 1 | 1 | 1 | 1 | 1 |
| | | Rate of Reaction | [%] | 16 | 50 | 27 | 28 | 7 | 13 |
| | | Enantiomeric Excess | [% e.e.] | 77 | 74 | 50 | 87 | 96 | 97 |

| | | | | EXAMPLE | | | | | |
|---|---|---|---|---|---|---|---|---|---|
| | | | | 7 | 8 | 9 | 10 | 11 | 12 |
| Asymmetric Catalyst Particles | Composition | N-tert-butyloxycarbonyl-o-(2-methacryloyloxyethylsuccinoyl)-trans-4-hydroxy-L-proline | [parts by mass] | | | | | | |
| | | N-tert-butyloxycarbonyl-o-(2-methacryloyloxyethylsuccinoyl)-cis-4-hydroxy-D-proline | [parts by mass] | | | | | | |
| | | N-tert-butyloxycarbonyl-o-(4-vinylbenzyl)-trans-4-hydroxy-L-proline | [parts by mass] | 10 | ← | ← | ← | ← | ← |
| | | Divinylbenzene | [parts by mass] | ← | ← | ← | ← | ← | ← |
| | | Isooctane | [parts by mass] | ← | ← | ← | ← | ← | ← |
| | | Dilauroyl Peroxide | [parts by mass] | ← | ← | ← | ← | ← | ← |
| | Particle Diameter Analysis | Apparatus Used: FPIA-3000, Sysmex | Average Particle Diameter [μm] | 2.764 | ← | ← | ← | ← | ← |
| | | | 50% Particle Diameter [μm] | 2.739 | ← | ← | ← | ← | ← |
| | | | Standard Deviation [μm] | 0.129 | ← | ← | ← | ← | ← |
| | | | CV Value [%] | 4.74 | ← | ← | ← | ← | ← |
| Colum Reactor Preparation Conditions | Column Size | | Outer Diameter [inch] | ← | ← | ⅜ | ← | ← | ← |
| | | | Inner Diameter [mm] | ← | ← | 7.6 | ← | ← | ← |
| | | | Length [mm] | ← | ← | 300 | ← | ← | ← |
| | Dispersion Medium | | Type | ← | ← | ← | ← | ← | ← |

TABLE 2-continued

| | | | | | | | | | |
|---|---|---|---|---|---|---|---|---|---|
| Column Reactor Reaction Conditions | Substrate Concentration | Flow Rate | [ml/min] | ← | ← | ← | ← | ← | ← |
| | | Maximum Pressure | [Mpa] | 25.7 | ← | 17.4 | ← | ← | ← |
| | | 4-Nitrobenzaldehyde | [wt %] | ← | ← | ← | ← | | |
| | | 3-Nitrobenzaldehyde | [wt %] | | | | | 13.7 | |
| | | 4-Trifluorobenzaldehyde | [wt %] | | | | | | 13.7 |
| | Mobile Phase Conditions | Water:Acetonitrile:Cyclohexanone | [Vol %] | ← | ← | ← | ← | ← | ← |
| | | Flow Rate | [ml/min] | 0.2 | 0.1 | 0.2 | 1.0 | 1.0 | 1.0 |
| | | Pressure | [Mpa] | 4.9 | 2.4 | 2.8 | 12.9 | 13 | 13.7 |
| | | Time | [hr] | 3.5 | 8 | 24 | 4 | 5 | 5 |
| Conditions for Analysis of Optically Active Compound | Analysis Target | 2-(Hydroxy(4-nitrophenyl)methyl)cyclohexan-1-one | Column Used for Analysis | AD-H | AD-H | AD-H | AD-H | | |
| | | 2-(Hydroxy(3-nitrophenyl)methyl)cyclohexan-1-one | | | | | | AD-H | |
| | | 2-(Hydroxy(4-trifluoromethylphenyl)methyl)cyclohexan-1-one | | | | | | | OD-H |
| | HPLC Conditions | Solvent (Hexane:Isopropyl Alcohol) | [Vol %] | 85:15 | 85:15 | 85:15 | 85:15 | 90:10 | 95:5 |
| | | Flow Rate | [ml/min] | 1 | 1 | 1 | 1 | 1 | 1 |
| | | Rate of Reaction | [%] | 12 | 22 | 43 | 13 | 6 | 24 |
| | | Enantiomeric Excess | [% e.e.] | 97 | 98 | 93 | 96 | 92 | 95 |

As can be seen from TABLE 2, the enantiomeric excess in each of Examples 5 to 12 in which N-tert-butyloxycarbonyl-O-(2-methacryloyloxyethylsuccinoyl)-cis-4-hydroxy-D-proline or N-tert-butyloxycarbonyl-O-(4-vinylbenzyl)-trans-4-hydroxy-L-proline was used was higher than the enantiomeric excess in each of Examples 1 to 4 in which N-tert-butyloxycarbonyl-O-(2-methacryloyloxyethylsuccinoyl)-trans-4-hydroxy-L-proline was used.

As can be seen from the comparison between Examples 5 and 6 and the comparison between Examples 7 and 8, by reducing the flow rate of the mobile phase during production of the optically active compound, the rate of the reaction is improved significantly. As can be seen from the comparison between Examples 9 and 10, by increasing the flow rate of the mobile phase during production of the optically active compound, the rate of the reaction decreases.

The following aspects <1> to <25> are also included in the present invention.

<1> An optically active compound production method using a column reactor prepared by charging a column for the column reactor with asymmetric catalyst particles, wherein the asymmetric catalyst particles are resin particles prepared from a monomer composition containing a monomer having a chiral source, and a reaction compound is introduced into the column reactor to bring the reaction compound into contact with the asymmetric catalyst particles, whereby the reaction compound is converted to an optically active compound.

<2> The production method according to <1>, wherein the asymmetric catalyst particles are resin particles prepared from a monomer composition containing, as the monomer having a chiral source, a proline derivative monomer having an unsaturated bond and further containing a radical polymerization initiator, the resin particles being capable of serving as a catalyst for an aldol reaction.

<3> The production method according to <1> or <2>, wherein the asymmetric catalyst particles are resin particles prepared by a micro-channel method including injecting the monomer composition into a continuous phase to form droplets of the monomer composition in the continuous phase and then heating the droplets to cause the proline derivative monomer having an unsaturated bond to undergo radical polymerization.

<4> The production method according to any one of <1> to <3>, wherein the proline derivative monomer having an unsaturated bond is O-acryloyl-trans-4-hydroxy-L-proline, O-acryloyl-cis-4-hydroxy-L-proline, O-methacryloyl-trans-4-hydroxy-L-proline, O-methacryloyl-cis-4-hydroxy-L-proline, O-(2-methacryloyloxyethylsuccinoyl)-trans-4-hydroxy-L-proline, O-(2-methacryloyloxyethylsuccinoyl)-cis-4-hydroxy-L-proline, N-tert-butyloxycarbonyl-O-acryloyl-trans-4-hydroxy-L-proline, N-tert-butyloxycarbonyl-O-acryloyl-cis-4-hydroxy-L-proline, N-tert-butyloxycarbonyl-O-methacryloyl-trans-4-hydroxy-L-proline, N-tert-butyloxycarbonyl-O-methacryloyl-cis-4-hydroxy-L-proline, N-tert-butyloxycarbonyl-O-(2-methacryloyloxyethylsuccinoyl)-trans-4-hydroxy-L-proline, N-tert-butyloxycarbonyl-O-(2-methacryloyloxyethylsuccinoyl)-cis-4-hydroxy-L-proline, O-acryloyl-trans-4-hydroxy-D-proline, O-acryloyl-cis-4-hydroxy-D-proline, O-methacryloyl-trans-4-hydroxy-D-proline, O-methacryloyl-cis-4-hydroxy-D-proline, O-(2-methacryloyloxyethylsuccinoyl)-trans-4-hydroxy-D-proline, O-(2-methacryloyloxyethylsuccinoyl)-cis-4-hydroxy-D-proline, N-tert-butyloxycarbonyl-O-acryloyl-trans-4-hydroxy-D-proline, N-tert-butyloxycarbonyl-O-acryloyl-cis-4-hydroxy-D-proline, N-tert-butyloxycarbonyl-O-methacryloyl-trans-4-hydroxy-D-proline, N-tert-butyloxycarbonyl-O-methacryloyl-cis-4-hydroxy-D-proline, N-tert-butyloxycarbonyl-O-(2-methacryloyloxyethylsuccinoyl)-trans-4-hydroxy-D-proline, N-tert-butyloxycarbonyl-O-(2-methacryloyloxyethylsuccinoyl)-cis-4-hydroxy-D-proline, N-tert-butyloxycarbonyl-O-(4-vinylbenzyl)-trans-4-hydroxy-L-proline, N-tert-butyloxycarbonyl-O-(4-vinylbenzyl)-cis-4-hydroxy-L-proline, N-tert-butyloxycarbonyl-O-(4-vinylbenzyl)-trans-4-hydroxy-D-proline, or N-tert-butyloxycarbonyl-O-(4-vinylbenzyl)-cis-4-hydroxy-D-proline.

<5> The production method according to any one of <1> to <3>, wherein the proline derivative monomer having an unsaturated bond is N-tert-butyloxycarbonyl-O-(2-methacryloyloxyethylsuccinoyl)-trans-4-hydroxy-L-proline, N-tert-butyloxycarbonyl-O-(2-methacryloyloxyethylsuccinoyl)-cis-4-hydroxy-D-proline, or N-tert-butyloxycarbonyl-O-(4-vinylbenzyl)-trans-4-hydroxy-L-proline.

<6> The production method according to any one of <1> to <4>, wherein the monomer composition further contains a monounsaturated or polyunsaturated compound monomer.

<7> The production method according to any one of <1> to <5>, wherein the monomer composition further contains divinylbenzene as a polyunsaturated compound monomer.

<8> The production method according to any one of <1> to <7>, wherein the reaction compound comprises a carbonyl compound having an α hydrogen.

<9> The production method according to any one of <1> to <7>, wherein the reaction compound comprises cyclohexanone as a carbonyl compound having an α hydrogen and one of 4-nitrobenzaldehyde, 3-nitrobenzaldehyde, and 4-trifluoromethylbenzaldehyde.

<10> The production method according to <9>, wherein the optically active compound is 2-(hydroxy(4-nitrophenyl)methyl)cyclohexan-1-one, 2-(hydroxy(3-nitrophenyl)methyl)cyclohexan-1-one, or 2-(hydroxy(4-trifluoromethylphenyl)methyl)cyclohexan-1-one.

<11> The production method according to any one of <1> to <10>, wherein the optically active compound converted from the reaction compound is further subjected to optical resolution in the column reactor.

<12> An optically active compound production method using a column reactor prepared by charging a column for the column reactor with asymmetric catalyst particles, wherein the asymmetric catalyst particles are resin particles prepared from a monomer composition containing, as a monomer having a chiral source, N-tert-butyloxycarbonyl-O-(2-methacryloyloxyethylsuccinoyl)-trans-4-hydroxy-L-proline, N-tert-butyloxycarbonyl-O-(2-methacryloyloxyethylsuccinoyl)-cis-4-hydroxy-D-proline, or N-tert-butyloxycarbonyl-O-(4-vinylbenzyl)-trans-4-hydroxy-L-proline and further containing a radical polymerization initiator, the resin particles being capable of serving as a catalyst for an aldol reaction, and a reaction compound comprising a carbonyl compound having an α hydrogen is introduced into the column reactor to bring the reaction compound into contact with the asymmetric catalyst particles, whereby the reaction compound is converted to an optically active compound.

<13> An optically active compound production method using a column reactor prepared by charging a column for the column reactor with asymmetric catalyst particles, wherein the asymmetric catalyst particles are resin particles prepared from a monomer composition containing, as a monomer having a chiral source, N-tert-butyloxycarbonyl-O-(2-methacryloyloxyethylsuccinoyl)-trans-4-hydroxy-L-proline, N-tert-butyloxycarbonyl-O-(2-methacryloyloxyethylsuccinoyl)-cis-4-hydroxy-D-proline, or N-tert-butyloxycarbonyl-O-(4-vinylbenzyl)-trans-4-hydroxy-L-proline and further containing a radical polymerization initiator, the resin particles being capable of serving as a catalyst for an aldol reaction, and reaction compounds comprising cyclohexanone as a carbonyl compound having an α hydrogen and one of 4-nitrobenzaldehyde, 3-nitrobenzaldehyde, and 4-trifluoromethylbenzaldehyde are introduced into the column reactor to bring the reaction compounds into contact with the asymmetric catalyst particles, whereby the reaction compounds are converted to an optically active compound, the optically active compound being 2-(hydroxy(4-nitrophenyl)methyl)cyclohexan-1-one, 2-(hydroxy(3-nitrophenyl)methyl)cyclohexan-1-one, or 2-(hydroxy(4-trifluoromethylphenyl)methyl)cyclohexan-1-one.

<14> An optically active compound production method using a column reactor prepared by charging a column for the column reactor with asymmetric catalyst particles, wherein:

the asymmetric catalyst particles are resin particles prepared from a monomer composition containing, as a monomer having a chiral source, N-tert-butyloxycarbonyl-O-(2-methacryloyloxyethylsuccinoyl)-trans-4-hydroxy-L-proline, N-tert-butyloxycarbonyl-O-(2-methacryloyloxyethylsuccinoyl)-cis-4-hydroxy-D-proline, or N-tert-butyloxycarbonyl-O-(4-vinylbenzyl)-trans-4-hydroxy-L-proline and further containing a radical polymerization initiator, the resin particles being capable of serving as a catalyst for an aldol reaction; and reaction compounds comprising cyclohexanone as a carbonyl compound having an α hydrogen and one of 4-nitrobenzaldehyde, 3-nitrobenzaldehyde, and 4-trifluoromethylbenzaldehyde are introduced into the column reactor to bring the reaction compounds into contact with the asymmetric catalyst particles, whereby the reaction compounds are converted to an optically active compound, the optically active compound being 2-(hydroxy(4-nitrophenyl)methyl)cyclohexan-1-one, 2-(hydroxy(3-nitrophenyl)methyl)cyclohexan-1-one, or 2-(hydroxy(4-trifluoromethylphenyl)methyl)cyclohexan-1-one; and the optically active compound is further subjected to optical resolution in the column reactor.

<15> An optically active compound production method using a column reactor prepared by charging a column for the column reactor with asymmetric catalyst particles, wherein:

the asymmetric catalyst particles are resin particles prepared by a micro-channel method including: injecting a monomer composition into a continuous phase to thereby form droplets of the monomer composition in the continuous phase, the monomer composition containing, as a monomer having a chiral source, N-tert-butyloxycarbonyl-O-(2-methacryloyloxyethylsuccinoyl)-trans-4-hydroxy-L-proline, N-tert-butyloxycarbonyl-O-(2-methacryloyloxyethylsuccinoyl)-cis-4-hydroxy-D-proline, or N-tert-butyloxycarbonyl-O-(4-vinylbenzyl)-trans-4-hydroxy-L-proline and further containing a radical polymerization initiator; and then heating the droplets to cause such a proline derivative monomer having an unsaturated bond to undergo radical polymerization, the resin particles being capable of serving as a catalyst for an aldol reaction;

reaction compounds comprising cyclohexanone as a carbonyl compound having an α hydrogen and one of 4-nitrobenzaldehyde, 3-nitrobenzaldehyde, and 4-trifluoromethylbenzaldehyde are introduced into the column reactor to bring the reaction compounds into contact with the asymmetric catalyst particles, whereby the reaction compounds are converted to an optically active compound, the optically active compound being 2-(hydroxy(4-nitrophenyl)methyl)cyclohexan-1-one, 2-(hydroxy(3-nitrophenyl)methyl)cyclohexan-1-one, or 2-(hydroxy(4-trifluoromethylphenyl)methyl)cyclohexan-1-one; and the optically active compound is further subjected to optical resolution in the column reactor.

<16> A column reactor comprising a column for the column reactor and asymmetric catalyst particles charged into the column, wherein the asymmetric catalyst particles are resin particles prepared from a monomer composition containing a proline derivative monomer having an unsaturated bond and a radical polymerization initiator, the resin particles being capable of serving as a catalyst for an aldol reaction.

<17> The column reactor according to <16>, wherein the asymmetric catalyst particles are prepared by a micro-channel method including injecting the monomer composition into a continuous phase to thereby form droplets of the monomer composition in the continuous phase and then heating the droplets to cause the proline derivative monomer having an unsaturated bond to undergo radical polymerization.

<18> The column reactor according to <16> or <17>, wherein the proline derivative monomer having an unsaturated bond is O-acryloyl-trans-4-hydroxy-L-proline, O-acryloyl-cis-4-hydroxy-L-proline, O-methacryloyl-trans-4-hydroxy-L-proline, O-methacryloyl-cis-4-hydroxy-L-proline, O-(2-methacryloyloxyethylsuccinoyl)-trans-4-hydroxy-L-proline, O-(2-methacryloyloxyethylsuccinoyl)-cis-4-hydroxy-L-proline, N-tert-butyloxycarbonyl-O-acryloyl-trans-4-hydroxy-L-proline, N-tert-butyloxycarbonyl-O-acryloyl-cis-4-hydroxy-L-proline, N-tert-butyloxycarbonyl-O-methacryloyl-trans-4-hydroxy-L-proline, N-tert-butyloxycarbonyl-O-methacryloyl-cis-4-hydroxy-L-proline, N-tert-butyloxycarbonyl-O-(2-methacryloyloxyethylsuccinoyl)-trans-4-hydroxy-L-proline, N-tert-butyloxycarbonyl-O-(2-methacryloyloxyethylsuccinoyl)-cis-4-hydroxy-L-proline, O-acryloyl-trans-4-hydroxy-D-proline, 0-acryloyl-cis-4-hydroxy-D-proline, O-methacryloyl-trans-4-hydroxy-D-proline, O-methacryloyl-cis-4-hydroxy-D-proline, O-(2-methacryloyloxyethylsuccinoyl)-trans-4-hydroxy-D-proline, O-(2-methacryloyloxyethylsuccinoyl)-cis-4-hydroxy-D-praline, N-tert-butyloxycarbonyl-O-acryloyl-trans-4-hydroxy-D-proline, N-tert-butyloxycarbonyl-O-acryloyl-cis-4-hydroxy-D-proline, N-tert-butyloxycarbonyl-O-methacryloyl-trans-4-hydroxy-D-proline, N-tert-butyloxycarbonyl-O-methacryloyl-cis-4-hydroxy-D-proline, N-tert-butyloxycarbonyl-O-(2-methacryloyloxyethylsuccinoyl)-trans-4-hydroxy-D-proline, N-tert-butyloxycarbonyl-O-(2-methacryloyloxyethylsuccinoyl)-cis-4-hydroxy-D-proline, N-tert-butyloxycarbonyl-O-(4-vinylbenzyl)-trans-4-hydroxy-L-proline, N-tert-butyloxycarbonyl-O-(4-vinylbenzyl)-cis-4-hydroxy-L-proline, N-tert-butyloxycarbonyl-O-(4-vinylbenzyl)-trans-4-hydroxy-D-proline, or N-tert-butyloxycarbonyl-O-(4-vinylbenzyl)-cis-4-hydroxy-D-proline.

<19> The column reactor according to any one of <16> to <18>, wherein the proline derivative monomer having an unsaturated bond is N-tert-butyloxycarbonyl-O-(2-methacryloyloxyethylsuccinoyl)-trans-4-hydroxy-L-proline, N-tert-butyloxycarbonyl-O-(2-methacryloyloxyethylsuccinoyl)-cis-4-hydroxy-D-proline, or N-tert-butyloxycarbonyl-O-(4-vinylbenzyl)-trans-4-hydroxy-L-proline.

<20> The column reactor according to any one of <16> to <19>, wherein the monomer composition further contains a monounsaturated or polyunsaturated compound monomer.

<21> The column reactor according to any one of <16> to <19>, wherein the monomer composition further contains divinylbenzene as a polyunsaturated compound monomer.

<22> A column reactor comprising a column for the column reactor and asymmetric catalyst particles charged into the column, wherein the asymmetric catalyst particles are resin particles prepared by: injecting a monomer composition into a continuous phase to thereby form droplets of the monomer composition in the continuous phase, the monomer composition containing, as a proline derivative monomer having an unsaturated bond, N-tert-butyloxycarbonyl-O-(2-methacryloyloxyethylsuccinoyl)-trans-4-hydroxy-L-proline, N-tert-butyloxycarbonyl-O-(2-methacryloyloxyethylsuccinoyl)-cis-4-hydroxy-D-proline, or N-tert-butyloxycarbonyl-O-(4-vinylbenzyl)-trans-4-hydroxy-L-proline and further containing a radical polymerization initiator; and then heating the droplets to cause the proline derivative monomer having an unsaturated bond to undergo radical polymerization, the resin particles being capable of serving as a catalyst for an aldol reaction.

<23> A column reactor production method comprising charging a column for a column reactor with asymmetric catalyst particles, wherein the asymmetric catalyst particles used are resin particles prepared from a monomer composition containing a proline derivative monomer having an unsaturated bond and a radical polymerization initiator, the resin particles being capable of serving as a catalyst for an aldol reaction.

<24> The production method according to <23>, wherein the asymmetric catalyst particles used are prepared by a micro-channel method including: injecting the monomer composition into a continuous phase to form droplets of the monomer composition in the continuous phase; and then heating the droplets to cause the proline derivative monomer having an unsaturated bond to undergo radical polymerization.

<25> A column reactor production method comprising charging a column for a column reactor with asymmetric catalyst particles, wherein the asymmetric catalyst particles used are resin particles prepared by: injecting a monomer composition into a continuous phase to thereby form droplets of the monomer composition in the continuous phase, the monomer composition containing, as a proline derivative monomer having an unsaturated bond, N-tert-butyloxycarbonyl-O-(2-methacryloyloxyethylsuccinoyl)-trans-4-hydroxy-L-proline, N-tert-butyloxycarbonyl-O-(2-methacryloyloxyethylsuccinoyl)-cis-4-hydroxy-D-proline, or N-tert-butyloxycarbonyl-O-(4-vinylbenzyl)-trans-4-hydroxy-L-proline and further containing a radical polymerization initiator; and then heating the droplets to cause the proline derivative monomer having an unsaturated bond to undergo radical polymerization, the resin particles being capable of serving as a catalyst for an aldol reaction.

INDUSTRIAL APPLICABILITY

According to the production methods of the present invention, an optically active compound can be produced using asymmetric catalyst particles. These methods can be easily applied to organic synthesis irrespective of its scale, and the reaction product can be separated from the catalyst without the need of a complicated separation operation.

The invention claimed is:

1. An optically active compound production method using a column reactor prepared by charging a column for the column reactor with asymmetric catalyst particles, wherein
the asymmetric catalyst particles have an average particle diameter of 1 to 10 μm as measured by a flow type particle image analysis method and are resin particles prepared from a monomer composition containing a monomer having a chiral source, and
a reaction compound is introduced into the column reactor to bring the reaction compound into contact with the asymmetric catalyst particles, whereby the reaction compound is converted to an optically active compound.

2. The production method according to claim 1, wherein the asymmetric catalyst particles are resin particles prepared from a monomer composition containing, as the monomer having a chiral source, a proline derivative monomer having an unsaturated bond and further containing a radical polymerization initiator, the resin particles being capable of serving as a catalyst for an aldol reaction.

3. The production method according to claim 2, wherein the asymmetric catalyst particles are resin particles prepared by a micro-channel method including injecting the monomer composition into a continuous phase to form droplets of the monomer composition in the continuous phase and then heating the droplets to cause the proline derivative monomer having an unsaturated bond to undergo radical polymerization.

4. The production method according to claim 2, wherein the proline derivative monomer having an unsaturated bond is O-acryloyl-trans-4-hydroxy-L-proline, O-acryloyl-cis-4-hydroxy-L-proline, O-methacryloyl-trans-4-hydroxy-L-proline, O-methacryloyl-cis-4-hydroxy-L-proline, O-(2-methacryloyloxyethylsuccinoyl)-trans-4-hydroxy-L-proline, O-(2-methacryloyloxyethylsuccinoyl)-cis-4-hydroxy-L-proline, N-tert-butyloxycarbonyl-O-acryloyl-trans-4-hydroxy-L-proline, N-tert-butyloxycarbonyl-O-acryloyl-cis-4-hydroxy-L-proline, N-tert-butyloxycarbonyl-O-methacryloyl-trans-4-hydroxy-L-proline, N-tert-butyloxycarbonyl-O-methacryloyl-cis-4-hydroxy-L-proline, N-tert-butyloxycarbonyl-O-(2-methacryloyloxyethylsuccinoyl)-trans-4-hydroxy-L-proline, N-tert-butyloxycarbonyl-O-(2-methacryloyloxyethylsuccinoyl)-cis-4-hydroxy-L-proline, O-acryloyl-trans-4-hydroxy-D-proline,O-acryloyl-cis-4-hydroxy-D-proline, O-methacryloyl-trans-4-hydroxy-D-proline, O-methacryloyl-cis-4-hydroxy-D-proline, O-(2-methacryloyloxyethylsuccinoyl)-trans-4-hydroxy-D-proline, O-(2-methacryloyloxyethylsuccinoyl)-cis-4-hydroxy-D-proline, N-tert-butyloxycarbonyl-O-acryloyl-trans-4-hydroxy-D-proline, N-tert-butyloxycarbonyl-O-acryloyl-cis-4-hydroxy-D-proline, N-tert-butyloxycarbonyl-O-methacryloyl-trans-4-hydroxy-D-proline,N-tert-butyloxycarbonyl-O-methacryloyl-cis-4-hydroxy-D-proline, N-tert-butyloxycarbonyl-O-(2-methacryloyloxyethylsuccinoyl)-trans-4-hydroxy-D-proline, N-tert-butyloxycarbonyl-O-(2-methacryloyloxyethylsuccinoyl)-cis-4-hydroxy-D-proline, N-tert-butyloxycarbonyl-O-(4-vinylbenzyl)-trans-4-hydroxy-L-proline, N-tert-butyloxycarbonyl-O-(4-vinylbenzyl)-cis-4-hydroxy-L-proline, N-tert-butyloxycarbonyl-O-(4-vinylbenzyl)-trans-4-hydroxy-D-proline, or N-tert-butyloxycarbonyl-O-(4-vinylbenzyl)-cis-4-hydroxy-D-proline.

5. The production method according to claim 2, wherein the proline derivative monomer having an unsaturated bond is N-tert-butyloxycarbonyl-O-(2-methacryloyloxyethylsuccinoyl)-trans-4-hydroxy-L-proline, N-tert-butyloxycarbonyl-O-(2-methacryloyloxyethylsuccinoyl)-cis-4-hydroxy-D-proline, or N-tert-butyloxycarbonyl-O-(4-vinylbenzyl)-trans-4-hydroxy-L-proline.

6. The production method according to claim 2, wherein the monomer composition further contains a monounsaturated or polyunsaturated compound monomer.

7. The production method according to claim 2, wherein the monomer composition further contains divinylbenzene as a polyunsaturated compound monomer.

8. The production method according to claim 2, wherein the reaction compound comprises a carbonyl compound having an α hydrogen.

9. The production method according to claim 2, wherein the reaction compound comprises cyclohexanone as a carbonyl compound having an α hydrogen and one of 4-nitrobenzaldehyde, 3-nitrobenzaldehyde, and 4-trifluoromethylbenzaldehyde.

10. The production method according to claim 9, wherein the optically active compound is 2-(hydroxy(4-nitrophenyl)methyl)cyclohexan-1-one, 2-(hydroxy(3-nitrophenyl)methyl)cyclohexan-1-one, or 2-(hydroxy(4-trifluoromethylphenyl)methyl)cyclohexan-1-one.

11. The production method according to claim 1, wherein the optically active compound converted from the reaction compound is further subjected to optical resolution in the column reactor.

12. An optically active compound production method using a column reactor prepared by charging a column for the column reactor with asymmetric catalyst particles, wherein
the asymmetric catalyst particles have an average particle diameter of 1 to 10 μm as measured by a flow type particle image analysis method and are resin particles prepared from a monomer composition containing, as a monomer having a chiral source, N-tert-butyloxycarbonyl-O-(2-methacryloyloxyethylsuccinoyl)-trans-4-hydroxy-L-proline, N-tert-butyloxycarbonyl-O-(2-methacryloyloxyethylsuccinoyl)-cis-4-hydroxy-D-proline, or N-tert-butyloxycarbonyl-O-(4-vinylbenzyl)-trans-4-hydroxy-L-proline, divinylbenzene as a polyunsaturated compound monomer, and further containing a radical polymerization initiator, the resin particles being capable of serving as a catalyst for an aldol reaction, and
a reaction compound comprising a carbonyl compound having an α hydrogen is introduced into the column reactor to bring the reaction compound into contact with the asymmetric catalyst particles, whereby the reaction compound is converted to an optically active compound.

13. An optically active compound production method using a column reactor prepared by charging a column for the column reactor with asymmetric catalyst particles, wherein
the asymmetric catalyst particles have an average particle diameter of 1 to 10 μm as measured by a flow type particle image analysis method and are resin particles prepared from a monomer composition containing, as a monomer having a chiral source, N-tert-butyloxycarbonyl-O-(2-methacryloyloxyethylsuccinoyl)-trans-4-hydroxy-L-proline, N-tert-butyloxycarbonyl-O-(2-methacryloyloxyethylsuccinoyl)-cis-4-hydroxy-D-proline, or N-tert-butyloxycarbonyl-O-(4-vinylbenzyl)-trans-4-hydroxy-L-proline, divinylbenzene as a polyunsaturated compound monomer, and further containing a radical polymerization initiator, the resin particles being capable of serving as a catalyst for an aldol reaction, and
reaction compounds comprising cyclohexanone as a carbonyl compound having an α hydrogen and one of 4-nitrobenzaldehyde, 3-nitrobenzaldehyde, and 4-trifluoromethylbenzaldehyde are introduced into the column reactor to bring the reaction compounds into contact with the asymmetric catalyst particles, whereby the reaction compounds are converted to an optically active compound, the optically active compound being 2-(hydroxy(4-nitrophenyl)methyl)cyclohexan-1-one, 2-(hydroxy(3-nitrophenyl)methyl)cyclohexan-1-one, or 2-(hydroxy(4-trifluoromethylphenyl)methyl)cyclohexan-1-one.

14. An optically active compound production method using a column reactor prepared by charging a column for the column reactor with asymmetric catalyst particles, wherein:

the asymmetric catalyst particles have an average particle diameter of 1 to 10μm as measured by a flow type particle image analysis method and are resin particles prepared from a monomer composition containing, as a monomer having a chiral source, N-tert-butyloxycarbonyl-O-(2-methacryloyloxyethylsuccinoyl)-trans-4-hydroxy-L-proline, N-tert-butyloxycarbonyl-O-(2-methacryloyloxyethylsuccinoyl)-cis-4-hydroxy-D-proline, or N-tert-butyloxycarbonyl-O-(4-vinylbenzyl)-trans-4-hydroxy-L-proline, divinylbenzene as a polyunsaturated compound monomer, and further containing a radical polymerization initiator, the resin particles being capable of serving as a catalyst for an aldol reaction; and reaction compounds comprising cyclohexanone as a carbonyl compound having an α hydrogen and one of 4-nitrobenzaldehyde, 3-nitrobenzaldehyde, and 4-trifluoromethylbenzaldehyde are introduced into the column reactor to bring the reaction compounds into contact with the asymmetric catalyst particles, whereby the reaction compounds are converted to an optically active compound, the optically active compound being 2-(hydroxy(4-nitrophenyl)methyl)cyclohexan-1-one, 2-(hydroxy(3-nitrophenyl)methyl)cyclohexan-1-one, or 2-(hydroxy(4-trifluoromethylphenyl)methyl)cyclohexan-1-one; and the optically active compound is further subjected to optical resolution in the column reactor.

15. An optically active compound production method using a column reactor prepared by charging a column for the column reactor with asymmetric catalyst particles, wherein:

the asymmetric catalyst particles have an average particle diameter of 1 to 10μm as measured by a flow type particle image analysis method and are resin particles prepared by a micro-channel method including: injecting a monomer composition into a continuous phase to thereby form droplets of the monomer composition in the continuous phase, the monomer composition containing, as a monomer having a chiral source, N-tert-butyloxycarbonyl-O-(2-methacryloyloxyethylsuccinoyl)-trans-4-hydroxy-L-proline, N-tert-butyloxycarbonyl-O-(2-methacryloyloxyethylsuccinoyl)-cis-4-hydroxy-D-proline, or N-tert-butyloxycarbonyl-O-(4-vinylbenzyl)-trans-4-hydroxy-L-proline divinylbenzene as a polyunsaturated compound monomer, and further containing a radical polymerization initiator; and then heating the droplets to cause such a proline derivative monomer having an unsaturated bond to undergo radical polymerization, the resin particles being capable of serving as a catalyst for an aldol reaction;

reaction compounds comprising cyclohexanone as a carbonyl compound having an α hydrogen and one of 4-nitrobenzaldehyde, 3-nitrobenzaldehyde, and 4-trifluoromethylbenzaldehyde are introduced into the column reactor to bring the reaction compounds into contact with the asymmetric catalyst particles, whereby the reaction compounds are converted to an optically active compound, the optically active compound being 2-(hydroxy(4-nitrophenyl)methyl)cyclohexan-1-one, 2-(hydroxy(3-nitrophenyl)methyl)cyclohexan-1-one, or 2-(hydroxy(4-trifluoromethylphenyl)methyl)cyclohexan-1-one; and the optically active compound is further subjected to optical resolution in the column reactor.

16. A column reactor production method comprising charging a column for the column reactor and asymmetric catalyst particles, wherein the asymmetric catalyst particles used have an average particle diameter of 1 to 10 μm as measured by a flow type particle image analysis method and are resin particles prepared from a monomer composition containing a proline derivative monomer having an unsaturated bond, divinylbenzene as a polyunsaturated compound monomer, and a radical polymerization initiator, the resin particles being capable of serving as a catalyst for an aldol reaction.

17. The production method according to claim 16, wherein the asymmetric catalyst particles used are prepared by a micro-channel method including: injecting the monomer composition into a continuous phase to form droplets of the monomer composition in the continuous phase; and then heating the droplets to cause the proline derivative monomer having an unsaturated bond to undergo radical polymerization.

18. A column reactor production method comprising charging a column for a column reactor with asymmetric catalyst particles, wherein the asymmetric catalyst particles used have an average particle diameter of 1 to 10 μm as measured by a flow type particle image analysis method and are resin particles prepared by: injecting a monomer composition into a continuous phase to thereby form droplets of the monomer composition in the continuous phase, the monomer composition containing, as a proline derivative monomer having an unsaturated bond, N-tert-butyloxycarbonyl-O-(2-methacryloyloxyethylsuccinoyl)-trans-4-hydroxy-L-proline, N-tert-butyloxycarbonyl-O-(2-methacryloyloxyethylsuccinoyl)-cis-4-hydroxy-D-proline, or N-tert-butyloxycarbonyl-O-(4-vinylbenzyl)-trans-4-hydroxy-L-proline, divinylbenzene as a polyunsaturated compound monomer, and further containing a radical polymerization initiator; and then heating the droplets to cause the proline derivative monomer having an unsaturated bond to undergo radical polymerization, the resin particles being capable of serving as a catalyst for an aldol reaction.

* * * * *